United States Patent
Anstey

(10) Patent No.: US 10,548,359 B2
(45) Date of Patent: Feb. 4, 2020

(54) MEDICAL/DENTAL/UTILITY GLOVE WITH ANTI-FATIGUE AND ERGONOMIC IMPROVEMENT

(71) Applicant: Paul Anstey, Los Angeles, CA (US)

(72) Inventor: Paul Anstey, Los Angeles, CA (US)

(*) Notice: Subject to any disclaimer, the term of this patent is extended or adjusted under 35 U.S.C. 154(b) by 0 days.

(21) Appl. No.: 15/792,402

(22) Filed: Oct. 24, 2017

(65) Prior Publication Data

US 2018/0295910 A1  Oct. 18, 2018

Related U.S. Application Data

(63) Continuation of application No. 14/930,791, filed on Nov. 3, 2015, now Pat. No. 9,801,422, which is a continuation of application No. 13/774,321, filed on Feb. 22, 2013, now Pat. No. 9,179,718.

(60) Provisional application No. 61/601,627, filed on Feb. 22, 2012.

(51) Int. Cl.
| | |
|---|---|
| *A41D 19/04* | (2006.01) |
| *A41D 19/00* | (2006.01) |
| *A41D 19/015* | (2006.01) |
| *A61B 42/00* | (2016.01) |
| *B29C 41/14* | (2006.01) |
| *A61B 17/00* | (2006.01) |
| *B29L 31/48* | (2006.01) |
| *B29L 31/00* | (2006.01) |

(52) U.S. Cl.
CPC ......... *A41D 19/0082* (2013.01); *A41D 19/00* (2013.01); *A41D 19/0062* (2013.01); *A41D 19/015* (2013.01); *A61B 42/00* (2016.02); *B29C 41/14* (2013.01); *A61B 2017/00424* (2013.01); *B29K 2995/0046* (2013.01); *B29L 2031/4864* (2013.01); *B29L 2031/753* (2013.01)

(58) Field of Classification Search
CPC .............. A41D 19/0058; A41D 19/015; A41D 19/0082; A41D 19/01523; A41D 19/00; A63B 71/143; A63B 71/146; A63B 71/141; A63B 2243/0004; A63B 2243/0008; A63B 2243/0025; A63B 2243/0029; A63B 2243/0045
See application file for complete search history.

(56) References Cited

U.S. PATENT DOCUMENTS

| | | | | |
|---|---|---|---|---|
| 2,036,413 A | * | 4/1936 | Herbruck | A41D 19/0062 174/5 SB |
| 3,283,338 A | * | 11/1966 | Landau | A41D 19/0062 2/161.6 |
| 3,601,816 A | * | 8/1971 | Pordes | A41D 19/0062 2/167 |

(Continued)

*Primary Examiner* — Robert H Muromoto, Jr.
(74) *Attorney, Agent, or Firm* — Merek, Blackmon & Voorhees, LLC

(57) ABSTRACT

The present invention is to an improved glove having both anatomically correlating stress relief zones and/or reinforced zones to add support in areas opposite the stress relief zones to keep bunching or slipping of the glove from interfering with the bending of the user's joints. The glove may have corrugated relief zones over some or all of the joints and knuckles of the hand, wherein the relief zones are formed of peaks and valleys. A relief zone can also be provided over the webbing between the thumb and the palm. The vertical or longitudinal relief zones provide for improved glove quality while keeping manufacturing difficulty and costs at a minimum.

6 Claims, 8 Drawing Sheets

(56) References Cited

U.S. PATENT DOCUMENTS

| | | | | |
|---|---|---|---|---|
| 5,323,490 A * | 6/1994 | Yarbrough | A41D 19/0062 | 2/161.7 |
| 6,044,493 A * | 4/2000 | Post | A41D 19/0065 | 2/16 |
| 6,272,687 B1 * | 8/2001 | Cunningham | A41D 19/0058 | 2/16 |
| 6,709,617 B2 * | 3/2004 | Wu | A61F 2/5046 | 264/102 |
| 6,760,923 B1 * | 7/2004 | Tate | A41D 19/0062 | 2/159 |
| 9,179,718 B2 * | 11/2015 | Anstey | A41D 19/015 | |
| 9,801,422 B2 * | 10/2017 | Anstey | A41D 19/015 | |
| 2002/0031628 A1 * | 3/2002 | Zumbrum | B32B 5/32 | 428/36.9 |
| 2002/0166156 A1 * | 11/2002 | Clark | A41D 19/0062 | 2/161.7 |
| 2002/0193488 A1 * | 12/2002 | Tao | C08J 3/243 | 524/418 |
| 2003/0204002 A1 * | 10/2003 | Osborn | C08J 3/226 | 524/270 |
| 2003/0230591 A1 * | 12/2003 | Jordan | B65D 83/0805 | 221/38 |
| 2004/0025222 A1 * | 2/2004 | Cass | A41D 19/01564 | 2/159 |
| 2004/0176512 A1 * | 9/2004 | Tao | C08K 3/22 | 524/418 |
| 2005/0035493 A1 * | 2/2005 | Flather | B29C 41/14 | 264/305 |
| 2005/0059764 A1 * | 3/2005 | Beck | B29C 67/24 | 524/425 |
| 2006/0026738 A1 * | 2/2006 | Kleinert | A41D 19/015 | 2/163 |
| 2006/0143767 A1 * | 7/2006 | Yang | A41D 19/015 | 2/16 |
| 2006/0212990 A1 * | 9/2006 | Mattesky | A41D 19/0006 | 2/161.6 |
| 2007/0226873 A1 * | 10/2007 | Mattesky | A41D 19/0006 | 2/159 |
| 2009/0007307 A1 * | 1/2009 | Le | A63B 71/143 | 2/19 |
| 2009/0307821 A1 * | 12/2009 | Chang | A41D 19/01588 | 2/21 |
| 2010/0005564 A1 * | 1/2010 | Park | A41D 19/02 | 2/163 |
| 2011/0118635 A1 * | 5/2011 | Yamamoto | A61H 1/02 | 601/5 |
| 2013/0263356 A1 * | 10/2013 | Jones | A41D 19/0013 | 2/163 |
| 2014/0059739 A1 * | 3/2014 | Gellis | A41D 19/015 | 2/168 |
| 2016/0120242 A1 * | 5/2016 | Thompson | A41D 19/001 | 2/161.6 |
| 2016/0366959 A1 * | 12/2016 | Hull | A41D 19/01517 | |

\* cited by examiner

MEDICAL/DENTAL/UTILITY GLOVE WITH ANTI-FATIGUE AND ERGONOMIC IMPROVEMENT

This application is a continuation of U.S. patent application Ser. No. 14/930,791, filed Nov. 3, 2015, entitled Medical/Dental/Utility Glove with Anti-Fatigue and Ergonomic Improvement, which application is a continuation of U.S. patent application Ser. No. 13/774,321, filed Feb. 22, 2014, entitled Surgical Glove with Stress Relief Features, which application claims the benefit of U.S. Provisional Application 61/601,627, filed Feb. 22, 2012, entitled Surgical Glove with Stress Relief Features. Each of these applications is incorporated herein by reference."

BACKGROUND OF THE INVENTION

1. Field of the Invention

The present application relates to an ergonometrically improved glove having areas near or within natural fold lines of a user's hand with stress relief features to provide lower resistance to flexing and anti-fatigue enhancements.

2. Description of the Prior Art

Latex and other medical gloves are used by medical and/or dental professionals to maintain a sanitary boundary between the medical staff (or other users/operators) and the patient. These gloves have also found their way into non-medical fields such as use by automotive workers, painters, and construction work to reduce the transfer of oils, paints, foams and chemicals onto the worker. The inventions described herein can also be used to increase the usability of sports gloves as well as general gloves for other purposes.

Medical gloves are typically of uniform thickness throughout the glove to maintain a low cost by simplifying production. This has led to a mismatch between the flex patterns of the gloves and the flexing of the hand of the wearer. When the wearer bends his fingers, for example, the glove must stretch unevenly along the wearer's joint and beyond as all hands differ in muscle and skeletal structure. The amount of force required to stretch the glove tends to cause fatigue in the hands of the wearer and can cause other discomfort such as constriction and uncomfortable rubbing/friction along the skin. Additionally, as the glove stretches on one side of the user, an area elsewhere on the hand may also experience bunching/sagging of the material as it fold on itself, for example, bunching beneath the joint of the fingers. In addition to the above disadvantages, this can reduce the tactile feel through the glove and interfere with grasping delicate instruments. A wearer thus often wears ill-fitting ("larger") gloves than the wearer's hand size to reduce fatigue with disadvantage of bunching at the fingertip or elsewhere than interferes with the grip and with the tactile feedback. What is needed is an economical, ergonomic glove that has anti-fatigue features and does not interfere with natural operation of the hands of the wearer.

Some efforts have been made in the past to provide stress relief areas. One such device is shown by Yarbrough in U.S. Pat. No. 5,323,490. A number of bellows are provided along two fingers of the glove to provide circumferential flex areas as well as too much flexure provided by the bellows causing the fingertips of the gloves to be too loose. Additionally, the portion of the bellows below the finger (palm side) is unnecessary and in the way causing a hindrance to an operator grasping an instrument, for example. Unfortunately, this does not remove the problem of the material bunching in the area opposite the flex zone.

A number of other gloves also provide various solutions, such as U.S. Pat. Nos. 3,283,338, and 6,962,739. However, none of these inventions and patents, taken either singly or in combination, is seen to describe the instant invention as claimed.

SUMMARY OF THE INVENTION

The present invention is to an improved glove having both anatomically correlating stress relief zones and/or reinforced zones to add support in areas opposite the stress relief zones to keep bunching or slipping of the glove from interfering with the bending of the user's joints. The glove may have corrugated relief zones over some or all of the joints and knuckles of the hand, wherein the relief zones are preferably formed of peaks and valleys parallel to the longitudinal axis of the fingers and thumb. A relief zone can also be provided over the webbing between the thumb and the palm. The vertical or longitudinal relief zones provide for improved glove quality while keeping manufacturing difficulty and costs at a minimum.

Accordingly, it is a principal object of a preferred embodiment of the invention to provide an improved glove having both anatomically correlating stress relief zones and reinforced zones to add support in areas opposite the stress relief zones to keep bunching or slipping of the glove from interfering with the bending of the user's joints.

It is another object of the invention to provide a glove having a number of support ridges or reinforcements to maintain the form of the glove as the hand bends and folds.

It is an object of the invention to provide a glove having a number of longitudinally ("vertically") aligned ridges on the glove to provide hand stretch relief zones, such as having folds in the relief zone substantially transverse to the axis of rotation of the fingers during flexing.

It is a further object of the invention to provide a glove having a number of stress relief portions to reduce the strain on the hands as the glove stretches around the bending hand and fingers.

Still another object of the invention is to provide a number of stress relief zones that have ribbed or accordion/diamond folds to provide stress-free stretching of the glove around the joints of the hand.

It is an object of the invention to provide a glove which allows the hand to assume its natural curvature and dramatically reduce stress and fatigue caused by high stress zones.

It is an object of the invention to provide improved elements and arrangements thereof in an apparatus for the purposes described which is inexpensive, dependable and fully effective in accomplishing its intended purposes.

These and other objects of the present invention will be readily apparent upon review of the following detailed description of the invention and the accompanying drawings. These objects of the present invention are not exhaustive and are not to be construed as limiting the scope of the claimed invention. Further, it must be understood that no one embodiment of the present invention need include all of the aforementioned objects of the present invention. Rather, a given embodiment may include one or none of the aforementioned objects. Accordingly, these objects are not to be used to limit the scope of the claims of the present invention.

BRIEF DESCRIPTION OF THE DRAWINGS

Similar reference characters denote corresponding features consistently throughout the attached drawings.

DETAILED DESCRIPTION OF THE PREFERRED EMBODIMENT(S)

The present invention according to at least one aspect is to an improve glove having stress relief zones and/or reinforced zones to increase the ergonomics, comfort and usability of the glove.

Figure 1:
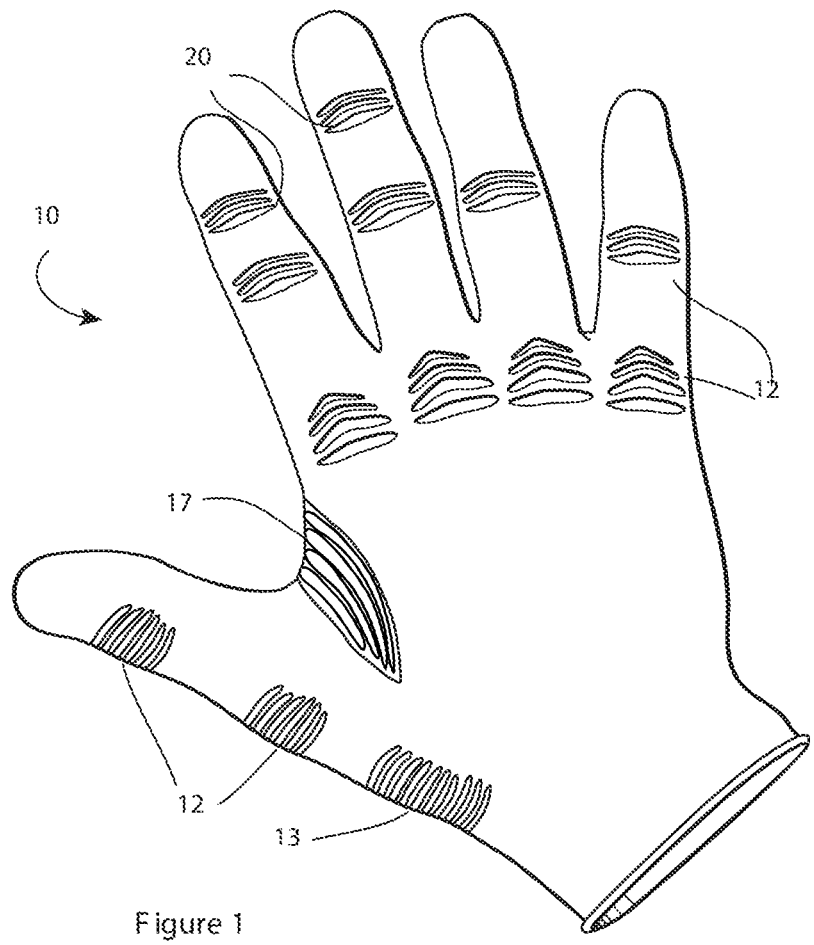
FIG. 1 is a back plan view of a glove according to at least one aspect of the invention.
Figure 2:
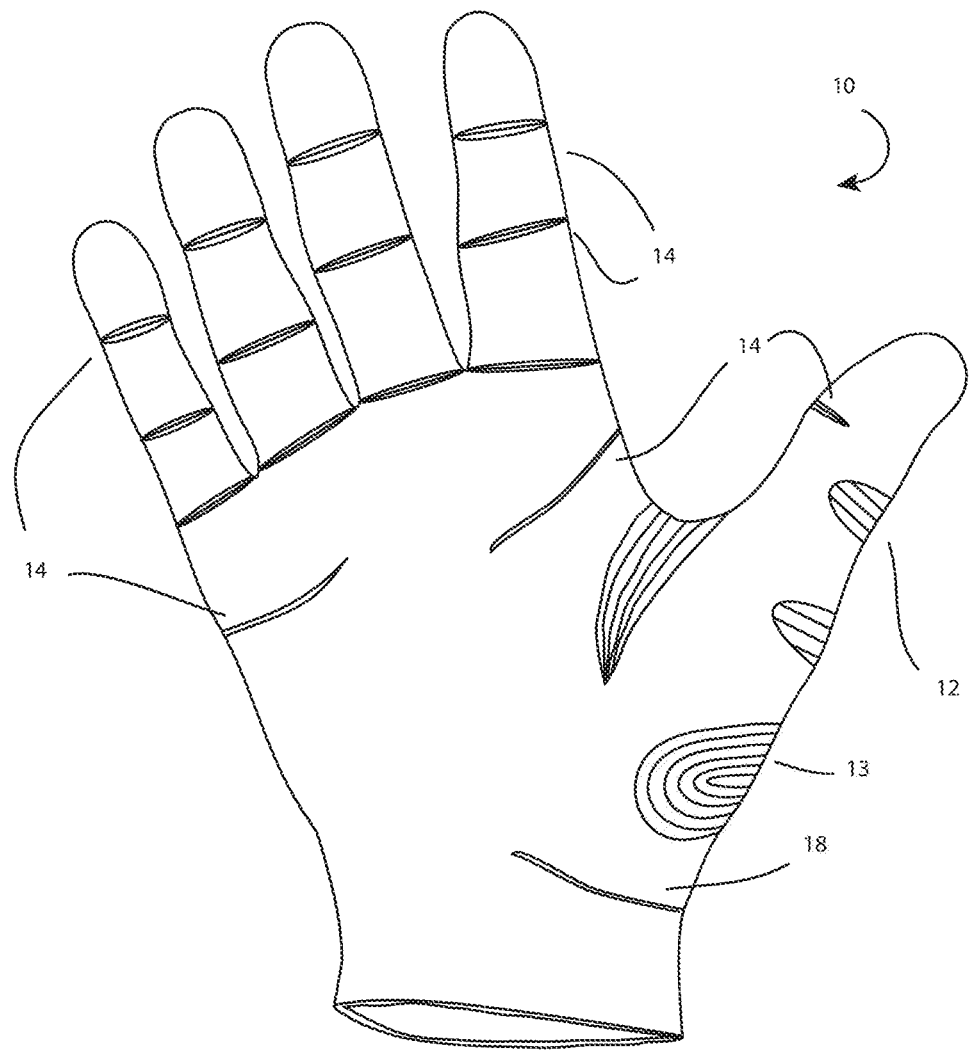
FIG. 2 is a front plan view of a glove according to at least one aspect of the invention.

FIG. 1 shows an exemplary embodiment of the back of a glove 10 according to at least one aspect of the invention. FIG. 2 shows the front (or palm side) of the glove. The different zones on the back are coincidentally stretch zones and the zones on the front are reinforced zones since the hand generally bends in only one direction, except for the thumb.

Figure 3:
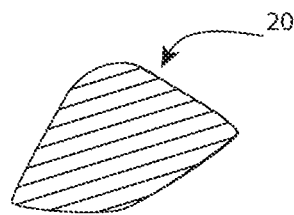
FIGS. 3 & 4 show an expanded view of expansion zones according to different preferred embodiments.
Figure 4:
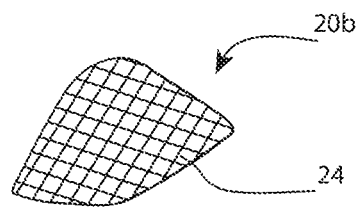

In practice, a glove would be constructed of a thin layer of uniform latex, nitril, vinyl or other material. According to a preferred embodiment of the invention, at least one stress relief area 12 is provided above the knuckles (knuckle joints, etc.) of the hand and located within the uniform thickness main glove portion. This stress relief area includes a ribbed or accordion fold (20, FIG. 3) or alternatively diamond cross link areas (20b, FIG. 4) so that as fingers of the hand bend, the stress area stretch with less resistance than the thin/uniform area of latex would have. The folds or ribs can "unfold" or "fold out" as the knuckle (or a joint) bends allow the material to expand a set distance before the material is "stretched" and may include elastic reinforcement in the rib or elsewhere to control expansion and contraction of the material and to maintain the integrity of the glove so that no tear or damage to the glove occurs. Alternatively, the folds could align with the fingers (i.e., transverse to the axis of the rotation/curling/flexing of the fingers) such as that shown in FIGS. 9-12 and explained later hereinunder. The expansion zone can be reinforced with crossing elastic fibers 24 or other material within the material to control the amount of stretching and the ability of the material to return to its contracted state, i.e., prevent over stretching and overall stabilizes the glove. This expansion reduces the amount of force necessary for the material of the glove to bend around the knuckles (or joints) of the hand as one or more fingers are curled to grasp a medical/dental instrument, for example. By providing the additional material in the relief zones, the wearer experiences less fatigue, since the fingers can move a greater distance before the glove material is stretched to accommodate movement or curling of the finger(s). The expansion zones are designed to provide less resistance to stretching or elongating along the length of the finger compared to the lateral ("circumferential") direction and compared to material outside the expansion zones of the glove. At least one rib may be provided in the expansion and/or reinforcement zone having enough lateral ("hoop") strength to ensure that the material beneath the knuckle or joint does not pull away from the finger and bunch up unnecessarily and to reduce the stretching in the circumferential direction.

An additional feature of the ribbed zones is that there is less constriction of the user's hand during operation. When an elastic material such as rubber stretches, it simultaneously narrows, the same as a rubber band will narrow as it is stretched. Since the glove is already adjacent the skin of the wearer, the stretching of the glove will narrow about the hand causing constriction and discomfort of the hand. By providing additional material in the expansion zones, the "expansion" of the glove involves the unfurling of the ribs or folds or diamond cross links instead of actually requiring significant "stretching" of the material thus avoiding the same constriction of the material.

Figure 10:
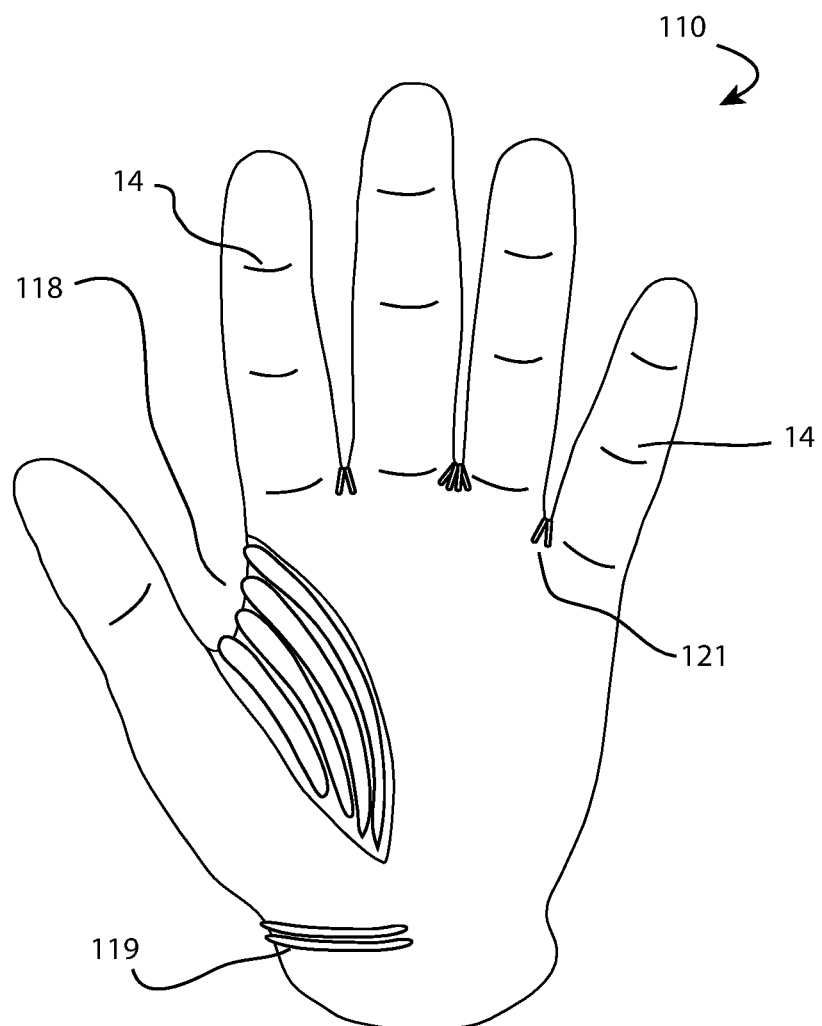

Another feature according to a preferred embodiment that can be used separately or with the expansion zones on the glove are stabilizer zones 14 as shown in FIG. 2 (and FIG. 10). These zones include a stiffener or support rib ("stabilizer") that is incorporated above or below the glove, but is preferably within the material or encapsulated in a similar material to the glove to appear within the material. For example, the stabilizer could be affixed on top of the glove material and then a similar latex later could be affixed over the stabilizer so that the stabilizer appears to be within the glove material. The stabilizer may be made of metal, but is preferably made of latex, vinyl nitrile, or other plastic or a dense rubber or similar material. The stabilizer may also be an area of extra thick base glove material, e.g., latex.

The stabilizer zones are located to cooperate with the expansion zones. The stabilizer zones may be connected directly to an expansion zone, but preferably are not extensions of the stretch zones, but are instead located in an associated position elsewhere on the glove. For example, for each expansion zone on the top of a finger knuckle there may be a stabilizer zone below the knuckle separated by an area of the uniform thickness glove portion ("base glove" portion). The stabilizer serves several functions. Firstly, the stabilizer has a length and width to maintain the fabric of the glove in the proper position and shape, such as maintaining a proper curvature about the finger when the finger is straight or bent. This prevents the glove from unduly constricting the finger as the joint is manipulated by separating the potentially loose material into small portions between each stabilizer. This prevents a large section of glove from pulling away from the hand underneath a finger. Secondly, the stabilizer has a length and width to control where the material bunches as a finger or other joint is bent. As material on top of the glove is stretched during bending of a finger, material beneath the joint is compressed. The compressed material will naturally fold and bunch in the zone below the finger. This may be in a location that prevents the user from properly grasping a tool or may destroy the tactile feel of the hand on the patient during a delicate operation. The stabilizer can provide a "non-bunching" zone beneath the finger by reducing the length or width of material between the stabilizers that is able to bunch and cause the material to bunch elsewhere or to fold neatly about the stabilizer. This helps emulate the folding of the finger naturally as the skin of the first and second joints of the finger do naturally around the knuckle of the finger.

The cooperation between the stabilizer and the ribbed zones is unique and provides a glove that acts as naturally similar to an ungloved hand as possible. Each expansion zone may have an associated, cooperating stabilizer. Additional stabilizers may be provided as shown in FIG. 2 across the palm below the pinkie or between the thumb and the forefinger. The groove between the thumb and the palm may have either or both an expansion area and a stabilizer area 17. Additional stabilizers or relief zones 14,18 may be provided along the thumb and below the thumb near the wrist. Stabilizers can also be placed on the last joint of the finger similar to the other knuckles and joints of the finger. The shape of the expansion zones may be modified as necessary, but is preferably a diamond shape with a larger base on the main knuckle or joint of the finger. The same shape may be provided at the other joints of the fingers, but preferably a modified elliptical shape drawing to a point at each end of the expansion zone is provided. Additional stabilizers and expansion zones may be placed in additional areas than those shown. One or more of the stabilizers or expansion zones shown in the drawing may be omitted or moved or resized as necessary. Ideally, a stabilizer is provided in an area where bunching would occur when a portion of the hand (or fingers) is moved and an expansion zone is provided where material of a glove would stretch during normal movement of a hand and/or finger. In a preferred embodiment, there is a stabilizer in the area that bunching would occur for each expansion zone in a "stretch" area of a joint.

FIGS. 1 and 2 show an example of one such glove with only some areas covered by expansion zones and stabilizers. Because the cost of manufacturing a glove increases with each expansion area or stabilizer added, the zones shown are felt to have the most impact.

Additional Preferred Embodiments

Figure 5:
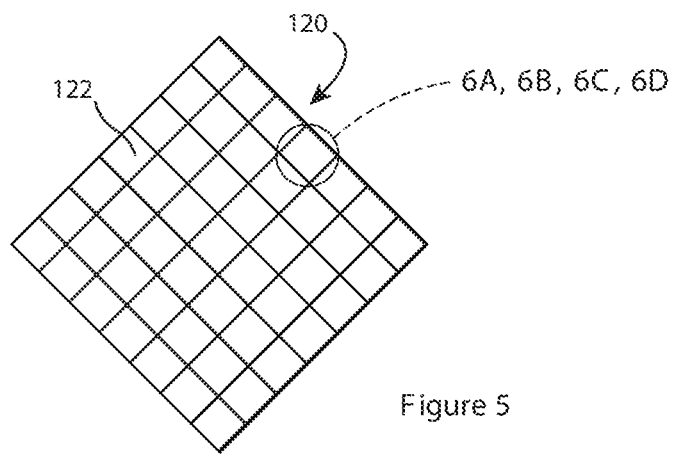
FIG. 5 shows a diagrammatic view of a diamond shape relief zone patterns for use on a glove.
Figure 6A:
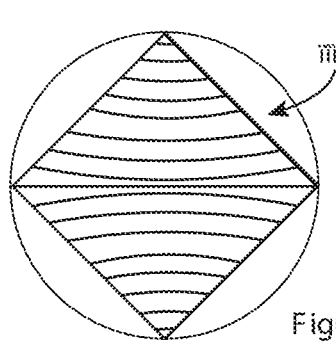
FIGS. 6A-D show diagrammatic views of a diamond shape relief zone patterns for use on a glove.
Figure 6C:
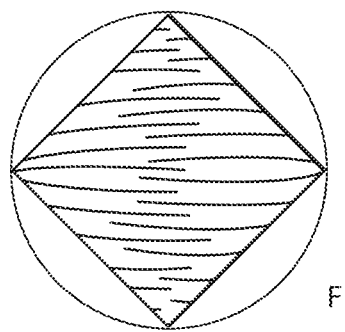
Figure 6B:
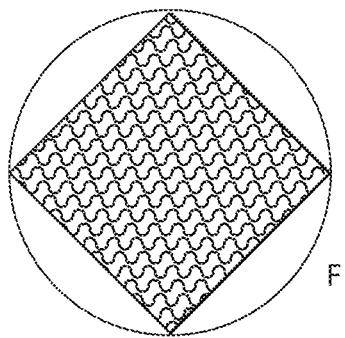
Figure 6D:
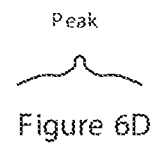

FIG. 5 shows an alternate stress relief zone construction 120. Each of the diamonds 122 (or the entire area 120) may be formed of a unique expansion pattern 124. FIGS. 6A, 6B and 6C show various alternative patterns that may be used. FIG. 6D is a side view of the expansion design in FIG. 6A and shows the peak elevation of each fiber in the expansion zone. In a preferred embodiment, each of the expansion patterns 6A-6C the lines represent a latex or material similar to the glove compositions and having a thickness approximately that of the glove and the areas between the lines are a thinner or easier to stretch material so that the expansion pattern stretches along a preferred contour. In 6A, the concentric wave like patterns from the top and bottom allow the material to stretch in predictable manners while being able to resume the original shape ("re-stabilize") when the finger and glove are no longer being flexed. In pattern 6B, an interlaced pattern allows for greater strength along the center of the pattern to aid the glove in regaining form between stretching. In pattern 6C, intricate parallel rows of offset waves allows the expansion pattern to stretch along pre-determined, multi-dimensional patterns such that the thicker latex "line" is always non-linear and has curved areas that can regain their original shape more easily. Alternatively, the patterns could be rotated 90 degrees to create vertical patterns having fold lines along the finger lines instead of transverse to the finger lines (that is transverse to a longitudinal axis of the finger(s)). The advantages of these configurations are discussed further below.

Figure 7A:
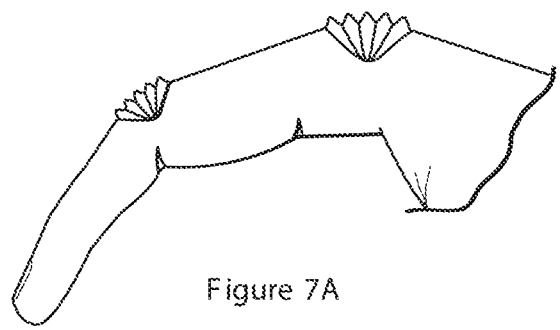
FIG. 7A-7B show diagrammatic views of relief zone profiles for use on a glove.
Figure 7B:
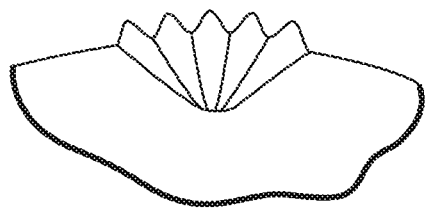
Figure 8A:
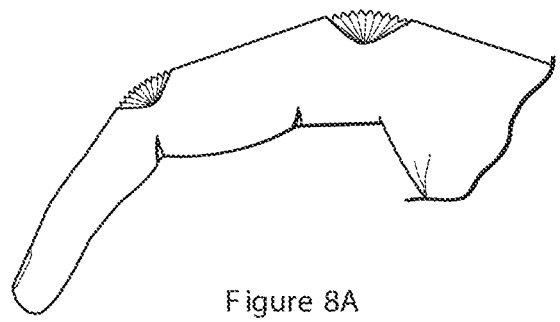
FIGS. 8A-8B show diagrammatic views of alternative relief zone patterns.
Figure 8B:
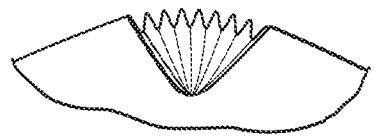

FIGS. 7 and 8 show concave and convex patterns. In FIG. 7, the thicker part of the material shown by the lines rises above the glove and the thinner areas are closer to the fingers as shown in profile 7B. FIGS. 8 and 8B show a concave design. In this design the thinner portions are further from the finger than the thicker portions giving an almost humped shape to the expansion pattern. Any of the relief zones shown in all of the figures could be concave or convex as needed.

Longitudinally ("Vertically") Aligned Stress Relief Zones

Figure 9:
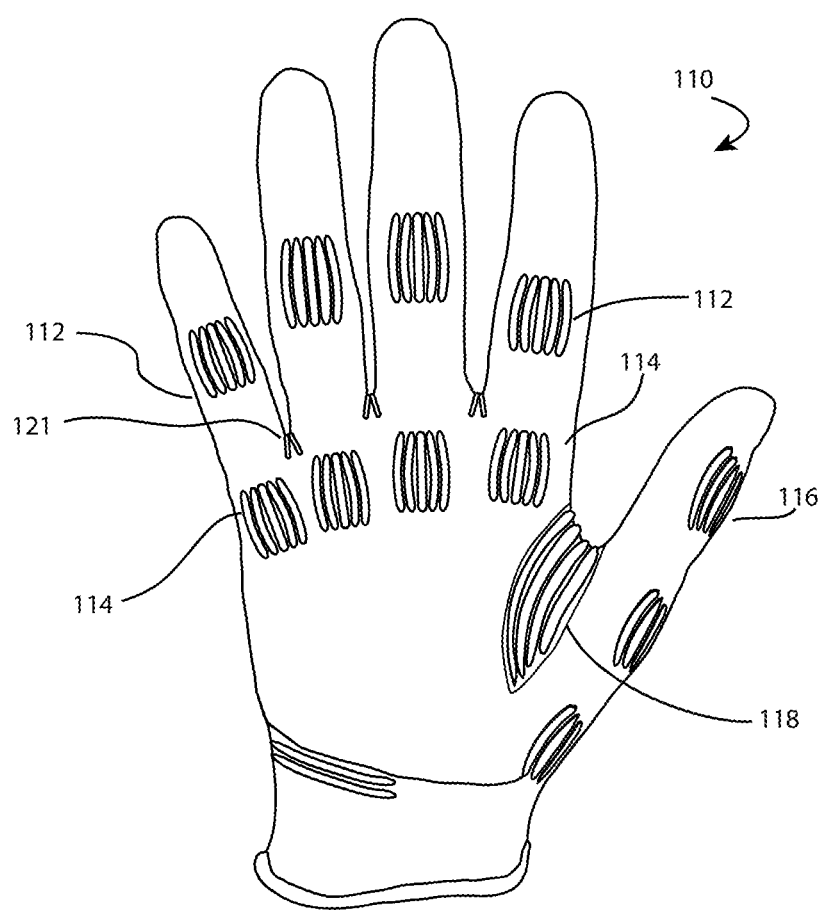
FIGS. 9 and 10 show the back and front of a glove according to a further embodiment of the glove.

FIGS. 9 and 10 shows an alternative, highly preferred embodiment of the invention. A glove 110 made of latex, nitryl, vinyl or similar material is shown. A number of relief zones 112, 114, 116, 118 are provide about the glove. A first set of relief zones 112 ("digit relief zones") are sited over the joint between the intermediate and proximal phalanges and each finger. A second set of relief zones 114 ("knuckle relief zones") are over the knuckles of the hand ("metacarpophalangeal joints") namely, over the joint between the proximal phalanges and metacarpals. A third set of relief zones 116 are over the joint of the thumb, namely between the distal and proximal phalanges of the thumb. A fourth relief zone 118 is over the webbing between the thumb and the index finger. An inter-finger relief zone 121 could also be provided between the fingers. Alternatively, an optional set of relief zones (20, FIG. 1) could be provided adjacent the joint below the distal phalanges of the fingers and/or thumb. Another relief zone (13, FIG. 1) could also be provided below the thumb, but preferably using a vertical relief pattern. A stabilizer zone (118) could alternatively or additionally be provided below the thumb.

The digit relief zones 112 and 116 provide for a low stress yielding of the glove along the finger and thumb as the finger and/or thumb (collectively referred to as "digit" or "digits") curls ("flexes") from the extended position to the curled or retracted position. The knuckle relief zones 114 provide an area of the glove to yield as the hand is balled into a fist. The webbing relief zone 119 provides for a low stress area of expansion as the thumb is extended away from the hand and provides freedom of movement as the thumb rotates in relation to the index finger.

A typical relief zone 112 is that on the joint of the middle finger. The relief zone is a break in the smooth "planar" glove. The relief zone provides an area that extends, stretches or bends more easily than the simple, uniform glove areas. The relief zone preferably consists of a corrugated area extending about 2.5 cm, but may vary according to the material or the amount of stretching required. Ideally, the corrugated area has around 4-6 folds of material with peaks in between separating the folds. The thickness of the glove in the corrugated area is constant and uniform with the rest of the glove. Where needed the glove could have thicker peaks or thinner folds to allow for more support or more stretching as needed. The folds are preferably uniform in length and width from one side to another. Alternatively, the folds in the middle could extend longer than the ones on the sides consistent with the stretching of the skin underneath the relief zone. In another embodiment, the central folds could extend parallel with the longitudinal axis of the respective finger while the outer folds are arced about the center fold to promote return of the folds to their original position when tension on the relief zone is released. The outer arced folds allow the outer folds to expand laterally about the finger as the finger is flexed to accommodate the three dimensional effect of the stretching and to reduce constriction of the finger. The outer most folds may be around 20% shorter than the central folds. An intermediate length fold having a length 10% shorter than the central fold can be located between the central and outermost folds where a wider relief zone is required. Alternatively, the width of each fold could be widened to provide a wider relief zone. Alternatively, the lengths of the folds could be formed such that the outer perimeter of the relief zone forms a diamond shape. The profile on the folds and peaks may be square, arcuate or sine waved so that the glove thickness remains constant throughout the folds at the time of construction. Where additional stretching is required, the folds can have an initial slight bowing away from the joint to accommodate more flexing of the joint before stretching of the material occurs, since there is no requirement for tactile feel around the back of the joint as opposed to the palm side of the glove where it is important to keep the glove material as close as possible to the hand to provide a "natural" feel.

Figure 11:
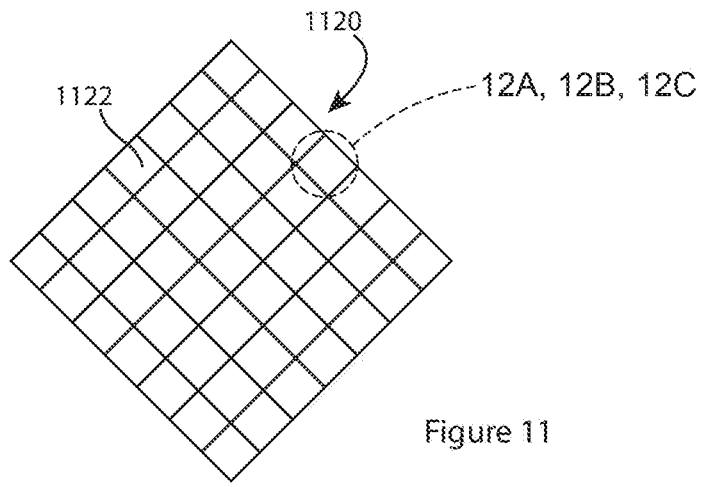
FIGS. 11 and 12A-C show diagrammatic views of a diamond shape relief zone patterns for use on a glove having vertical relief patterns.
Figure 12A:
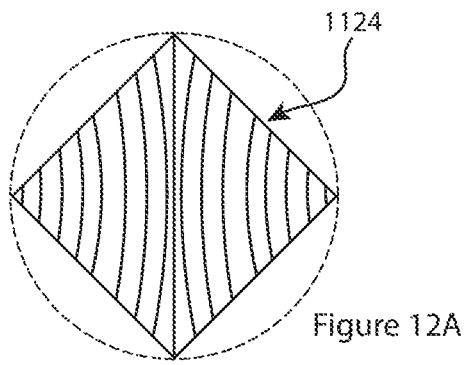
Figure 12C:
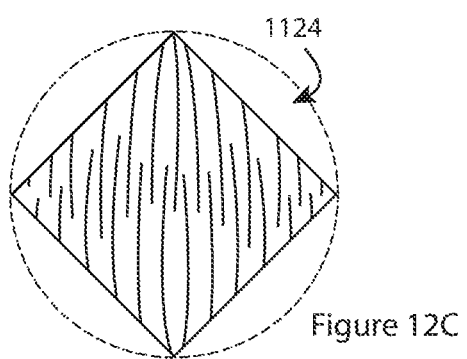
Figure 12B:
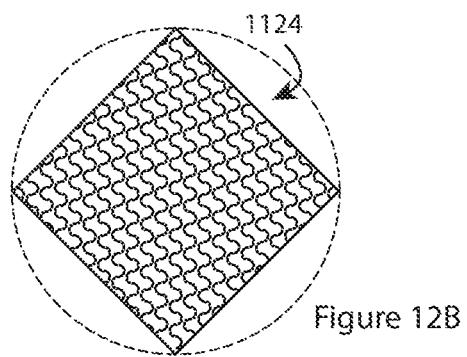

As shown in FIGS. 9 and 10, the glove consists mainly of the back (FIG. 9) of the glove having a number of relief zones, while the front (FIG. 10) of the glove has mainly only the webbing relief zone 118 extending on to the front of the glove. As described above, the glove may have additional stabilizer zones as well. The glove may also use any of the shapes or patterns of the above described glove, including the diamond patterns in place of or in addition to some or all of the vertical relief zones described below. FIG. 11 shows once such diamond pattern 1124 that could be used on the glove of FIG. 9. The vertical patterns of FIGS. 12A-C could be used to replace the entire diamond 1120 or could form the pattern for each diamond 1122. The folds could also run at any other angle to the finger as needed to suit the particular location, material or function required.

The digit relief zones 112,114 are preferably elongated and run in a direction ("vertical") along the longitudinal axis of the finger. Although it is unexpected and contrary to popular conceptions to have relief zones with a longitudinal axis parallel to the digits, there are several advantages to this construction. The main advantage is that it allows for a simple construction of the gloves, especially when using a dip mold to maintain a very low cost, highly flexible glove.

It is important to maintain the cost of medical/utility gloves at a very low level so that they can be disposed of at the end of a procedure or when changing tasks, etc. Gloves having flexible zones would be of reduced value if their costs were significantly higher than gloves in use today. One low cost method of making gloves of latex or similar material is by using a dip mold. The current invention is not limited to the method of manufacture, but one such method is to build a base mold of greenstone, glass, ceramic or other similar or known material. The mold relief zones can be channeled into the mold as vertical grooves of a size and shape configured for the size and shape desired on the product gloves. The amount, length and shape of the grooves will depend on the glove material and the glove size (small, medium, large etc.) among other considerations. A silicone or plaster mold ("cast") can then be created using known methods from the greenstone master. The cast can then be dipped into the latex to form the glove, typically after heating the cast for some types of rubber or plastic. Additional dippings can be used to add layers to the glove to create a more durable or reusable glove such as a utility or kitchen glove. The glove can then be peeled from the cast after it has dried, cured or set.

When the cast is dipped into the latex or similar material, excess material can drip off the glove back into the pool of latex under the force of gravity (or air pressure, etc.). The use of vertical grooves allows the latex to freely drip off the glove during this process. Horizontal groves or ridges can impede this flow causing pooling of the material and thus uneven coatings along the glove, which can detract from the operation of the relief zones. The vertical grooves can thus provide optimum glove construction, while minimizing costs and obviating the need for further manufacturing steps to prevent pooling, etc.

The vertical relief zones 112,114 parallel to the longitudinal axis of the digits are still able to reduce the amount of effort that it takes to bend the fingers or make a fist versus other gloves of similar thickness and material. As a finger bends the corrugations in the relief zone can spread apart to allow the joint to push up into one or more folds of the relief zone. The corrugation effect provides more material within the relief zones without having "thicker" material in the relief zone, providing the ability for the relief zones to accommodate more movement/bending of the fingers without causing as much tension in the glove itself. In a preferred embodiment, the glove material is of a uniform thickness even throughout the relief zone, but could be thinner in portions of the folds. The relief zones preferably extend approximately 120 to 140 degrees around the circumference of the finger, but may extended to a more or less degree according to the glove material, intended use, etc. However, it has been found that spreading less than half way around the finger allows for enough stress relief without causing interference between the fingers and without causing loss of tactile feel beneath the finger.

The relief zone instead moves materials out ("spreads out") of the way and around the finger instead of immediately stretching material out of the way of the joint as a prior art glove does. This parting of the corrugated relief zones allows the finger to expand into the space defined by the corrugated material with zero or very minimal tension created in the glove and thus low pressure on or minimal constriction of the fingers. The fingers and hand will thus experience less fatigue than if the fingers are fighting against the pull of the material as the fingers flex and curl.

In a similar fashion, the webbing relief area 118, reduces the amount of stress in the glove and thus the pressure on the thumb muscles and webbing of the hand as the thumb moves away from the hand or rotates. Unlike the finger areas of the glove that wrap around the joint as the fingers curl, the webbing area of the glove is being pulled away (instead of around) from the web area. In a preferred embodiment, the webbing relief zone 118 extends from the back of the hand around to the palm area of the hand to provide for additional relief of the webbing area throughout the entire motion of the thumb. The relief zone also allows the glove material to keep in close contact with the web of the hand instead of pulling out of contact as a normal glove can do. This allows the user to wear a closer fit glove rather than relying on the extra material of a larger glove to allow for free motion of the hand and thumb within the glove.

In a preferred embodiment the digit relief zones on the fingers 112 contain grooves/folds that are approximately 3-6 mm deep for a small glove size, depending on the glove material, number of folds, etc. and preferably 2-2.5 cm in length, but at least 1 cm in length. The depth of the web relief zone on the thumb 118 is preferably 4-6 mm deep.

While this invention has been described as having a preferred design, it is understood that it is capable of further modifications, uses and/or adaptations of the invention following in general the principle of the invention and including such departures from the present disclosure as come within the known or customary practice in the art to which the invention pertains and as may be applied to the central features hereinbefore set forth, and fall within the scope of the invention and the limits of the appended claims. It is therefore to be understood that the present invention is not limited to the sole embodiment described above, but encompasses any and all embodiments within the scope of the following claims.

I claim:

1. A method of making a protective glove having stress relief areas, comprising:

providing a mold in the shape of a human hand, sand hand having a smooth surface over a majority of the hand form of the mold;

said mold having a back section in the shape of a back of a hand; finger portions in the shape of the fingers of a hand; and a thumb portion in the shape of a thumb of a hand;

providing a relief section within the finger section by forming a plurality of channels on the mold over the finger portion of the mold, at least one of said channels being substantially parallel to the longitudinal axis of the finger portion of the mold;

heating said mold;

contacting said mold with a flowable elastic material to coat said mold with the elastic material;

allowing said elastic material to harden against the mold to form an elastic glove.

2. The method of making a protective glove of claim 1, wherein said elastic material is selected from the group of latex, nitryl; and vinyl.

3. The method of making a protective glove of claim 1, wherein said elastic material in said channel form a relief zone over said finger area.

4. The method of making a protective glove of claim 1, wherein said relief section includes at a central channel and two outer channels adjacent to said central channel.

5. The method of making a protective glove of claim 4, wherein said central channel is parallel to the longitudinal axis of said hand section and each outer channel is an arcuate channel curving about said central channel.

6. The method of making a protective glove of claim 1, further comprising:

providing a stabilizer section within the finger section by forming a plurality of stabilizer channels on the mold on the opposite side of the finger section from the relief section channels, wherein at least one of said stabilizer channels is substantially transverse to the longitudinal axis of the finger portion of the mold.

* * * * *